United States Patent [19]

Shimp et al.

[11] Patent Number: 5,702,677
[45] Date of Patent: Dec. 30, 1997

[54] SPHERICAL HYDROXYAPATITE PARTICLES AND PROCESS FOR THE PRODUCTION THEREOF

[75] Inventors: Lawrence A. Shimp; Peter J. Renkema, both of Leiden, Netherlands

[73] Assignee: Osteotech, Inc., Eatontown, N.J.

[21] Appl. No.: 679,611

[22] Filed: Jul. 10, 1996

[51] Int. Cl.$^6$ ............................................. C01B 25/32
[52] U.S. Cl. ..................... 423/308; 23/313 R; 264/117; 423/309; 423/311
[58] Field of Search .................... 423/308, 309, 423/311; 264/117; 23/313 R

[56] References Cited

U.S. PATENT DOCUMENTS

| | | | |
|---|---|---|---|
| 4,497,075 | 2/1985 | Niwa et al. | 423/308 |
| 4,518,430 | 5/1985 | Brown et al. | |
| 4,952,323 | 8/1990 | Nakabayashi et al. | |
| 5,053,212 | 10/1991 | Constanz et al. | |
| 5,149,368 | 9/1992 | Liu et al. | |
| 5,152,836 | 10/1992 | Hirano et al. | |
| 5,205,928 | 4/1993 | Inoue et al. | 423/308 |
| 5,217,699 | 6/1993 | Tagaya et al. | 423/308 |
| 5,441,635 | 8/1995 | Ichitsuka et al. | |

FOREIGN PATENT DOCUMENTS

| | | |
|---|---|---|
| 416761 | 3/1991 | European Pat. Off. |
| 543765 | 5/1993 | European Pat. Off. |
| 2227176 | 7/1990 | United Kingdom . |
| WO93/15721 | 8/1993 | WIPO . |

OTHER PUBLICATIONS

Misek, et al., "The Inflammatory Response to Different Shaped Hydroxylapatite Particles Implanted in Soft Tissue," 9th Annual Meeting of the Society of Biomaterials, Apr. 27–May 1, 1983.

Cacitite 4060 Dense Nonresorbable Bone Graft Material for Filling Periodontal and Pontic Area Defects, Calcitek, Inc., Carlsbad, California (Apr. 1988).

Orthomatrix Non–resorbable Hydroxylapatite Bone Graft Substitute, Lifecore Biomedical, Inc., Chaska, Minnesota (Dec. 1992).

Frialit Hydroxylapatit–Keramik, Friedricksfeld Medizin—Technik (date unknown).

Hy-Apatite, An Unique Calciumhydroxyapatite, Euro Crystals (date unknown).

Alveograf Non–resorbable Bone–Grafina Implant Material, Cook–Waite (date unknown).

OsteoGraft Hydroxylapatite, Ceramed (date unknown).

Yogyo–Kyokai–Shi, vol. 95, No. 2, pp. 284–285 (1987) (No month available).

Biomaterials, vol. 10, pp. 634–638 (1989) (No month available).

*Primary Examiner*—Wayne Langel
*Attorney, Agent, or Firm*—Elliot M. Olstein; Raymond J. Lillie

[57] ABSTRACT

A process for producing spherical, non-porous hydroxyapatite particles having a size which does not exceed 250 microns and having a density of at least 3.00 g/cc. The process comprises agglomerating in the presence of water as the only additive hydoxyapatite powder feedstock having a purity of at least 97%, and having metallic impurities which do not exceed 500 ppm, to form hydroxyapatite particles having a size which does not exceed 350 microns. The particles are then dried and then sintered at a temperature from about 1,100° C. to about 1,200° C. to provide spherical, non-porous hydoxyapatite particles which do not exceed 250 microns and having a density of at least 3.00 g/cc. Such particles have a variety of medical uses, including bone replacement, implant coatings, and dental applications such as alveolar ridge augmentation, root extraction site fillings, restoration of periodontal osseous lesions, and soft tissue augmentations.

10 Claims, No Drawings

SPHERICAL HYDROXYAPATITE PARTICLES AND PROCESS FOR THE PRODUCTION THEREOF

This invention relates to hydroxyapatite particles and to the production of such particles. More particularly, this invention relates to the production of small, dense, and spherical hydroxyapatite particles.

Hydroxyapatite particles having a small particle size (such as less than 500 microns), and which have a high density (such as greater than or equal to 3.02 g/cc) and are spherical, have a variety of uses. Such particles may be used as implant materials, in bone replacement, as coatings of implants, and in dental applications such as alveolar ridge augmentations, root extraction site fillings, and restoration of periodontal osseous lesions. Such particles also may be injected into the body. The particles also show maximum resistance to degradation.

Existing processes for making hydroxyapatite particles or granules provide products that are either high density or spherical, but not both, unless the particle size is large.

Dense particulate or granulate products are made by (i) drying and sintering a hydroxyapatite filter cake, followed by grinding (or possibly with an intermediate calcining and grinding grinding step); or (ii) pressing and sintering powder, followed by grinding. In all cases, a dense form of hydroxyapatite is produced and then ground to size. The grinding process provides particles that are shaped irregularly and are not spherical. Further processing, such as tumbling, may polish the particles, but such processing does not make the particles spherical.

Spherical particles in general are made from powders by an agglomeration process. The agglomerated particles then are sintered and sieved to size. The agglomerated particles, however, are highly porous and become dense only through the sintering process. Impurities in the hydroxyapatite or crystalline size or geometry can prevent one from forming hydroxyapatite particles having a sufficient density.

Conventional agglomeration processes rely upon the use of binders or the use of a solution of the material being agglomerated to increase density. Such methods are not effective with hydroxyapatite. Binders may interfere with the sintering process, even if organic binders which leave no mineral residue upon firing are used. Forming a solution of hydroxyapatite is not feasible unless acid is added to the solution. The acid, however, changes the chemistry of the hydroxyapatite such that it is no longer hydroxyapatite.

It is therefore an object of the present invention to provide a process for the production of non-porous hydroxyapatite particles that are spherical, dense, and have a size which enables such particles to be injected easily.

In accordance with an aspect of the present invention, there is provided a process for producing non-porous hydroxyapatite particles. The particles have a density of at least 3.00 g/cc, preferably at least 3.01 g/cc, more preferably at least 3.02 g/cc, are spherical, and have a size which in general does not exceed 250 microns. The particles are formed from a hydroxyapatite powder having a purity of at least 97%, and which contains metallic impurities in an amount which does not exceed 500 ppm. In general, such powder is formed by reacting calcium hydroxide with phosphoric acid, in the presence of water but in the absence of dispersants and surfactants, to form a slurry of hydroxyapatite. The slurry then is dried to provide a hydroxyapatite powder having a purity of at least 97%, and containing metallic impurities in an amount which does not exceed 500 ppm. Preferably, such hydroxyapatite powder, prior to the agglomeration thereof, has an average particle size under 25 microns.

The hydroxyapatite powder then is subjected to agglomeration, preferably with water as the only additive that is employed during the agglomeration process. No binders or other organic materials are employed during the agglomeration process. The agglomeration process provides hydroxyapatite granules which have a size which in general does not exceed 350 microns. The hydroxyapatite granules are dried, and then sintered at a temperature of from about 1,100° C. to about 1,200° C. in order to obtain non-porous spherical hydroxyapatite particles having the above-mentioned desired size and density.

The term "non-porous" as used herein means that the porosity of the hydroxyapatite particles does not exceed 5%. The term "spherical" as used herein means that the particles have a minimum width which is at least 90% of the maximum width. Applicants have found surprisingly that, if one agglomerates hydroxyapatite powder which has a purity of at least 97%, and has metallic impurities which do not exceed 500 ppm, one can obtain hydroxypatite particles which are non-porous, as well as spherical and having a desired density.

The hydroxyapatite powder is produced by reacting calcium hydroxide with phosphoric acid. Preferably, the calcium hydroxide has a purity of at least 95%, more preferably, at least 97%, and has metallic impurities which do not exceed 500 ppm. During such reaction, no dispersants or surfactants are added to the reaction mixture. Preferably, the reaction is carried out in a non-metallic reaction vessel, thereby preventing contamination of the reaction mixture with metal. In one embodiment, the reaction is carried out in a polypropylene tank fitted with an air-operated membrane pump for recirculation and mixing.

In general, the calcium hydroxide is suspended in water in the reaction vessel, and phosphoric acid diluted in water is added to the vessel by means of a peristaltic pump. Once the reaction is completed, the slurry is allowed to circulate prior to drying. If desired, more water may be added to the reaction vessel before spray drying.

Spray drying may be effected by connecting a feed hose to the reactor. The connection between the hose and the reactor may include a filter, such as a 75 micron filter. The slurry may be spray dried through any suitable spray drier known to those skilled in the art. Upon spray drying, the hydroxyapatite powder is sieved through an appropriate screen, such as, for example, a 90 micron screen, in order to remove any lumps.

The resulting hydroxyapatite powder, in general, has a purity of at least 97%, preferably of at least 98%, more preferably of at least 99%. The hydroxyapatite powder may include metallic impurities which do not exceed 500 ppm, and preferably do not exceed 350 ppm, and more preferably do not exceed 300 ppm. Most preferably, the metallic impurities do not exceed 200 ppm. Such powder preferably also has an average particle size under 25 microns.

The hydroxyapatite powder, after spray drying, then is subjected to agglomeration. The hydroxyapatite powder is added to an agglomerator, and water is added slowly. The water is added at a rate which will not cause excessive lumping or cause the granules to be broken down. When the granulation process appears to be finished, which may be determined visually or by a quantitative measure such as the torque output of the agglomerator motor, the process is stopped and the granulate is removed. The hydroxyapatite granules may be air-dried, dried in a warm oven, or dried in a fluid bed granulator.

After the granules are dried, they are sieved into the desired particle size. Based upon shrinkage during firing or sintering, in order to obtain particles having a desired particle size of 75 to 125 microns, it is preferred that the dried granulate be sieved to obtain granules having a size of from 90 to 212 microns.

The granulate then is sintered to obtain hydroxyapatite particles having a desired particle size. In general, the granulate is sintered at a temperature of from about 1,100° C. to about 1,200° C., preferably at about 1,200° C. The granulate may be sintered in the air, or in an inert atmosphere, with or without water addition.

The resulting hydroxyapatite particles have a variety of uses including, but not limited to, implant materials, implant coatings, dental applications such as alveolar ridge augmentations, mandibular augmentations, root extraction site fillings, and restoration of periodontal osseous lesions. Such hydroxyapatite particles also may be used in the treatment of urinary incontinence as a urinary sphincter augmentation material. The hydroxyapatite particles also may be used for filling soft tissue voids, for creating soft tissue blebs, for the treatment of unilateral vocal cord paralysis, and for breast implants.

In instances of urinary incontinence, such as stress incontinence in women, or after a prostatectomy in men, it is necessary to compress the urethra to assist the sphincter muscle in closing to avoid leakage of urine from the bladder.

The hydroxyapatite particles of the present invention may be injected into the urethral wall to add bulk and localize compression to the sphincter muscle/urethra, thereby reducing the lumen size through one or more injections of the hydroxyapatite particles and thus substantially reduce or eliminate urinary stress incontinence due to incompetent sphincters in females and males.

The hydroxyapatite particles can also be used in filling and smoothing out soft tissue defects such as pock marks or scars. Further use of the hydroxyapatite particles may be for intracordal injections of the laryngeal voice generator by changing the shape of thsi soft tissue mass. The procedure involves delivering the hydroxyapatite particles to the site of treatment, preferably by injection.

The hydroxyapatite particles can also be used for breast implants, and can be encased in a suitable shell made of a polymeric material such as polyurethanes, ethylene-propylene diene monomers, ethylene-propylene rubbers, polyolefins, and silicone elastomers. It can also be used without a shell because the hydroxyapatite particles do not migrate and remain in a particular area or bolus.

The hydroxyapatite particles may be administered to a patient via implantation or via injection. In general, the hydroxyapatite particles are administered in an amount of from about 5 g to about 20 g, preferably from about 10 g to about 15 g. The exact dosage of particles to be administered may be dependent upon a variety of factors, including the age, weight, and sex of the patient, and the size and severity of the defect being treated, or the extent of the augmentation being performed. The particles may be injected in combination with an acceptable physiological carrier. Acceptable physiological carriers include, but are not limited to, glycerol and cellulose polysaccharide gels. In one embodiment, the cellulose polysaccharide gel includes water, glycerin, and sodium carboxymethylcellulose. Other polysaccharides which may be included in the gel include, but are not limited to, cellulose, agar methylcellulose, hydroxypropyl methylcellulose, ethylcellulose, microcrystalline cellulose, oxidized cellulose, and other equivalent materials.

The invention now will be described with respect to the following examples; however, the scope of the present invention is not intended to be limited thereby.

EXAMPLE 1

6,500 grams of high purity calcium hydroxide was suspended in 95 liters of demineralized water in a recirculating plastic tank. 5,960 grams of high purity (85%) phosphoric acid, diluted to about 40% with demineralized water, was added over a three-hour period to the calcium hydroxide suspension. The rate of addition then was lowered, and the remaining phosphoric acid (about 600 grams) was added over a one-hour period.

After 16 hours of mixing, 20 liters of demineralized water was added to the slurry, and the reaction slurry was spray-dried in three hours in a Niro Production Minor spray dryer with a rotary atomizer. The inlet temperature was 200° C., and the outlet temperature was approximately 80° C. The hydroxyapatite powder collected from the spray dryer was sieved through a 90 micron sieve. The average particle size was 16 microns.

The hydroxyapatite powder had a purity of at least 97% and had the following metallic elements in the following concentrations:

| Element | Concentration, ppm |
| --- | --- |
| Cd | <1 |
| Zn | <1 |
| Al | 15 |
| Ba | 0.5 |
| Fe | 17 |
| Mn | 0.5 |
| K | <50 |
| Mg | 110 |
| Na | 80 |
| Sr | 11 |
| Si | 20 |

Granulation was carried out in batches of about 750 grams each in a Niro Pell Mix agglomerator. To each batch, 490 grams of water was added slowly over about a 25 minute period as the mixing impeller speed was increased periodically from 175 rpm to 650 rpm. Granulation was completed by mixing the material for about 10 more minutes at an impeller speed of 750 rpm. The granulate was dried in a Strea-1 fluid bed dryer at about 80° C. The dried granulate was sieved to obtain a yield of 27% of particles having a size greater than 212 microns, 61% of the particles having a size from 90 microns to 212 microns, and 12% of the particles having a size less than 90 microns.

The sieved granulate was sintered in an electric furnace at 1,200° C. for 10 hours. The furnace was open to the atmosphere, and about one liter of water was added slowly to a stream of air that was fed to the furnace during sintering. After sintering, the granulate had a particle size of 75 to 125 microns, and a density between 3.02 g/cc and 3.05 g/cc.

EXAMPLE 2

The procedure of Example 1 was repeated, except that water was not added during sintering. After sintering, the granulate had a particle size of 75 to 125 microns, and the density of the particles was 3.02 g/cc.

EXAMPLE 3

The procedure was the same as that of Example 1, except that sintering was carried out in an inert furnace constantly flushed with a mixture of nitrogen and hydrogen gas at a ratio of nitrogen to hydrogen gas of 90:10 and with water addition. The results were the same as those in Example 1.

EXAMPLE 4

The procedure of Example 1 was repeated, except that 500 grams of a polyammonium dispersant (Dispex) was added to the reaction slurry of calcium hydroxide and phosphoric acid after 90% of the acid was added, and the final acid addition time was not reduced. The yield of granulate (prior to sintering) having a size from 90 to 212 microns was 6%. The density of the product after sintering was between 3.02 g/cc and 3.05 g/cc.

EXAMPLE 5

The procedure of Example 4 was repeated, except with the sintering conditions of Example 3. The granulate yield prior to sintering of particles having a size from 90 to 212 microns was 6%, and the sintered product had a density of 3.02 g/cc.

EXAMPLE 6

The procedure of Example 1 was repeated, except that 4.9 grams (1% by weight) of an organic binder (methylcellulose) was added to the water used in the granulation process. The yield of particles having a size from 90 to 212 microns prior to sintering was 7%. The density of the particles after sintering was 3.08 g/cc.

EXAMPLE 7

The procedure of Example 6 was repeated, except that the sintering conditions of Example 3 were employed. The yield of the granules prior to sintering having a size from 90 to 212 microns was 7%, and the density of the sintered product was greater than 3.08 g/cc.

EXAMPLE 8

The procedure of Example 6 was repeated, except that sintering was carried out in air at 1,200° C. without water addition. The yield of granules prior to sintering having a size from 90 to 212 microns was 7%, and the density of the final sintered product was from 3.05 to 3.08 g/cc.

EXAMPLE 9

The procedure of Example 8 was repeated, except that the sintering temperature was 1,100° C. The yield of granules prior to sintering having a size from 90 to 212 microns was 7%, and the density of the sintered product was 3.08 g/cc.

EXAMPLE 10

The procedure of Example 6 was repeated, except that 500 grams of a polyammonium dispersant (Dispex) was added to the reaction slurry after 90% of the acid was added, and the final acid addition time was not reduced. The yield of granules prior to sintering which had a size from 90 to 212 microns was zero, and 98% of the granulate was greater than 1 mm in diameter.

EXAMPLE 11

The procedure from Example 1 was repeated, except that sintering was effected at 1,100° C. The sintered product had a density of 2.99 to 3.02 g/cc.

EXAMPLE 12

The procedure of Example 1 was repeated, except that low-purity calcium hydroxide and low-purity phosphoric acid were reacted to form a hydroxyapatite granulate product having the following metallic elements in the following amounts:

| Element | Concentration, ppm |
| --- | --- |
| Cd | <1 |
| Zn | 4 |
| Al | 360 |
| Ba | 2 |
| Fe | 195 |
| Mn | 6 |
| K | 50 |
| Mg | 4,000 |
| Na | 120 |
| Sr | 104 |
| Si | 700 |

The yield of the granules prior to sintering having a size of 90 to 212 microns was 75%. The density of the sintered product was 2.96 g/cc.

EXAMPLE 13

The procedure of Example 2 was repeated, except that low-purity calcium hydroxide and low-purity phosphoric acid were reacted. The yield of granules prior to sintering having a size from 90 to 212 microns was 75%. The density of the final sintered product less than 2.96 g/cc.

EXAMPLE 14

The procedure of Example 3 was repeated, except that low-purity calcium hydroxide and low-purity phosphoric acid were reacted. The yield of granules prior to sintering having a size of 90 to 212 microns was 75%, and the density of the final sintered product was less than 2.96 g/cc.

EXAMPLE 15

The procedure of Example 12 was repeated, except that 500 grams of Dispex dispersant was added to the reaction slurry after 90% of the acid was added, and the final acid addition time was not reduced. The yield of granulate prior to sintering having a size from 90 to 212 microns was zero, with almost the entire granulate being greater than 1.5 mm in diameter. The density of the sintered particles were less than 2.96 g/cc.

EXAMPLE 16

The procedure of Example 12 was repeated, except that 4.9 grams (1% by weight) of the methylcellulose binder was added prior to the water used in the granulation process. The yield of granules prior to sintering having a size of 90 to 212 microns was 1%, and the density of the sintered particles was less than 2.96 g/cc.

EXAMPLE 17

The procedure of Example 16 was followed, except that sintering was carried out in accordance with the procedure of Example 3. The yield of granules prior to sintering having a size of 90 to 212 microns was 1%, and the density of the sintered product was 2.99 to 3.02 g/cc.

EXAMPLE 18

The procedure of Example 12 was repeated, except that 4.9 grams (1% by weight) of methylcellulose binder was added to the water used in the granulation process. The yield of granules prior to sintering having a size of 90 to 212 microns was zero, with all of the granules being greater than 0.5 mm in diameter. The density of the sintered product was less than 2.96 g/cc.

EXAMPLE 19

The procedure of Example 4 was repeated, except that sintering was carried out in air without water addition. The yield of granules prior to sintering having a size of 90 to 212 microns was 6%. The density of the sintered product was from 2.99 to 3.02 g/cc.

EXAMPLE 20

The procedure of Example 19 was repeated, except that sintering was carried out at 1,100° C. The yield of granules prior to sintering having a size of 90 to 212 microns was 6%. The density of the sintered product was 2.96 g/cc.

It is to be understood, however, that the scope of the present invention is not to be limited to the specific embodiments described above. The invention may be practiced other than as particularly described and still be within the scope of the accompanying claims.

What is claimed is:

1. A process for producing spherical, non-porous hydroxyapatite particles having a size which does not exceed 250 microns, and having a density of at least 3.00 g/cc, comprising:

agglomerating in the presence of water as the only additive a hydroxyapatite powder feedstock having a purity of at least 97% and having metallic impurities which do not exceed 500 ppm, to form hydroxyapatite particles having a size which does not exceed 350 microns;

drying said hydroxyapatite particles; and sintering said dried hydroxyapatite particles at a temperature of from about 1,100° C. to about 1,200° C. to provide spherical, non-porous hydroxyapatite particles having a size which does not exceed 250 microns and having a density of at least 3.00 g/cc.

2. The process of claim 1 wherein said hydroxyapatite powder has a purity of at least about 98%.

3. The process of claim 1 wherein said hydroxyapatite powder has metallic impurities which do not exceed 350 ppm.

4. The process of claim 3 wherein said hydroxyapatite powder has metallic impurities which do not exceed 300 ppm.

5. The process of claim 1 wherein said spherical non-porous hydroxyapatite particles have a size of from about 75 microns to about 125 microns.

6. The process of claim 1 wherein said spherical hydroxyapatite particles are sintered at a temperature of about 1,200° C.

7. The process of claim 1 wherein said hydroxyapatite powder feedstock, prior to agglomeration, has an average particle size under 25 microns.

8. The process of claim 1 wherein said spherical non-porous hydroxyapatite particles have a density of at least 3.02 g/cc.

9. Hydroxyapatite particles produced according to the process of claim 1.

10. A process for producing spherical, non-porous hydroxyapatite particles having a size which does not exceed 250 microns, and having a density of at least 3.00 g/cc, comprising:

reacting calcium hydroxide having a purity of at least 95%, and having metallic impurities which do not exceed 500 ppm, with phosphoric acid, in the absence of dispersants or surfactants, to provide a hydroxyapatite powder feedstock having a purity of at least 97% and having metallic impurities which do not exceed 500 ppm;

agglomerating said hydroxyapatite feedstock in the presence of water as the only additive to form hydroxyapatite particles having a size which does not exceed 350 microns;

drying said hydroxyapatite particles; and sintering said dried hydroxyapatite particles at a temperature of from about 1,100° C. to about 1,200° C. to provide spherical, non-porous hydroxyapatite particles having a size which does not exceed 250 microns and having a density of at least 3.00 g/cc.

* * * * *